United States Patent [19]
Goh et al.

[11] Patent Number: 5,415,171
[45] Date of Patent: May 16, 1995

[54] PHASE IMAGING AND MYOCARDIAL PERFORMANCE

[75] Inventors: Christiana Goh, Montclair; Hewlett E. Melton, Jr., Sunnyvale, both of Calif.

[73] Assignee: Hewlett-Packard Company, Palo Alto, Calif.

[21] Appl. No.: 104,308

[22] Filed: Aug. 9, 1993

[51] Int. Cl.$^6$ .............................................. A61B 8/00
[52] U.S. Cl. ........................... 128/660.07; 128/661.04
[58] Field of Search ..................... 128/660.01, 660.02, 128/660.06, 660.07, 661.03, 661.04, 661.07–661.10, 696

[56] References Cited

U.S. PATENT DOCUMENTS

| | | | |
|---|---|---|---|
| 4,881,549 | 11/1989 | Rhyne | 128/660.07 |
| 5,111,825 | 5/1992 | Nishiyama et al. | 128/661.09 |
| 5,170,170 | 12/1992 | Soumekh | 342/179 |
| 5,224,481 | 7/1993 | Ishihara et al. | 128/660.07 |
| 5,241,473 | 8/1993 | Ishihara et al. | 128/660.01 X |
| 5,246,006 | 9/1993 | Kanda et al. | 128/661.09 |
| 5,257,626 | 11/1993 | Pelc et al. | 128/661.09 X |
| 5,285,788 | 2/1994 | Arenson et al. | 128/660.07 X |
| 5,289,820 | 3/1994 | Beach et al. | 128/661.07 |
| 5,325,859 | 7/1994 | Ishihara et al. | 128/660.07 |
| 5,355,887 | 10/1994 | Iizuka et al. | 128/660.07 X |

OTHER PUBLICATIONS

Chu, C. H. et al, "Detecting LV Endocardial and Epicardial Boundaries by Digital Two-Dimensional Echocardiography", IEEE Med Imaging Trans. vol. 7 No. 2 Jun. 1988 pp. 81–89.

Kuecherer, Helmut F., et al., "Two-dimensional Echocardiographic Phase Analysis," *Circulation*, vol. 85, No. 1, Jan. 1992, pp. 130-142.

Wickline, Samuel A., et al., "The dependence of myocardial ultrasonic integrated backscatter on contractile performance," *Circulation*, vol. 72, No. 1, Jul. 1985, pp. 183-192.

*Primary Examiner*—Francis Jaworski

[57] ABSTRACT

A method and system for monitoring performance of a heart includes forming a time series of frames of echocardiographic data. The time series may be for a systolic interval, but longer intervals are also possible. The frames of the time series have sets of corresponding data points with respect to specific sites of a patient's heart. For each set of corresponding data points, a time domain signal as a function of a selected scalar is determined, thereby yielding a time domain signal which varies with frame-to-frame variations of the selected scalar. The scalar has a physiological significance to the contractile state or the motion of the myocardium. Mean squared speed, root mean squared speed, mean squared rate of signal change, integrated backscatter, correlation area, and echocardiographic signal data magnitude are suitable scalars. For each time domain signal, a phase angle is obtained to assign a pixel value to an image data point. The pixel values are utilized to generate either a gray-scale two-dimensional image or a time series of cardiac performance.

19 Claims, 4 Drawing Sheets

PHASE IMAGING AND MYOCARDIAL PERFORMANCE

TECHNICAL FIELD

The present invention relates generally to monitoring heart performance and more particularly to methods and systems for echocardiographic imaging.

BACKGROUND ART

Two types of clinical tools for monitoring cardiac operation are systems for recording electrical behavior and systems for imaging mechanical behavior. With regard to electrical behavior, cardiac depolarization occurs in a wave to induce a contraction sequence. As depolarization spreads throughout the muscle cells of the heart, electrical currents spread to surrounding tissues, creating potential differences on the body surface. An electrocardiogram (ECG) utilizes a number of leads to measure and record these potentials. ECG data is used for the diagnosis of some pathological processes. However, the ECG is limited in the detail of information it can provide.

One area of research into imaging the cardiac motion is radionuclide ventriculography. Radionuclide ventriculography involves injection of a radioactive tracer into the bloodstream. The radioactive tracer emits radiation in the form of a gamma ray or an x-ray when spontaneously decaying to a more stable form. Dynamic cardiac images can then be generated by displaying time-accumulated radioactivity from a gamma camera on a pixel-by-pixel basis. Cardiac contraction sequence information is obtained using phase imaging. In phase imaging, the time-accumulated radioactivity of each data point in the planar blood-pool image is the scalar plotted over a cardiac cycle. A functional image is then generated from the phase of the first harmonic of the time activity curve at each pixel value. One drawback of radionuclide ventriculography is that contraction sequence information is limited to the endocardial border of the heart, which is the only region of the heart in contact with the blood pool.

Another area of research into imaging cardiac mechanical motion is high-speed digital subtraction echocardiography, which has been tried specifically for the direct visualization of the focus of ventricular premature contraction. This research is described in Ishihara et al., "Direct Visualization of the Forces of Ventricular Premature Contraction by High-Speed Digital Subtraction Echocardiograph," Abstract of Paper to be considered for presentation at American College of Cardiology, 40th Annual Scientific Session. B-mode echocardiograms were obtained at a rate of 164 frames per second. This allowed the crude visualization of myocardial contraction, with the wave of contraction progressing approximately ⅓ down the septum between each frame. Sectors of 30° limit visualization only to the septum. Visualization of cardiac contraction in other portions of the heart, such as the apex or the free ventricular wall, have either not been attempted or are not possible given the existing technology. Similar approaches for delineating the contraction sequence involve the subtraction of paired angiography data frames. Digital subtraction angiography has been attempted for the assessment of the ventricular contraction sequence and location of accessory pathway sites in patients with Wolff-Parkinson-White syndrome.

The idea of phase imaging has also been applied to echocardiography, as described in Kuecherer et al., "Two-Dimensional Echocardiographic Phase Analysis," Circulation, Vol. 85, No. 1, pages 130–142, January 1992. Data obtained from transthoracic echocardiograms was recorded on a video tape. The study included acquiring a 16-frame digital cine loop from the video tape and performing a phase analysis based upon pixel intensity of the video data. The phase analysis yielded images which allowed localization of accessory pathways with a high reliability, but details of cardiac operation were not obtainable. Therefore, further improvements to the study of cardiac performance are desired.

It is an object of the present invention to provide a method and system for improved delineation of the sequence of mechanical motion of a heart.

SUMMARY OF THE INVENTION

The above object has been met by an echocardiographic system and method which utilize cardiac performance data that are specifically related to physiological dynamics of heart performance. That is, information regarding cardiac operation is obtained by monitoring and analyzing a variable, hereinafter referred to as a "scalar," which varies predictably with the cardiac cycle in a manner that is physiologically significant. Suitable scalars are those that vary with contractile state or with motion of the myocardium.

The method includes transmitting ultrasonic wave energy into a patient and receiving echo signals reflected from the heart of the patient. The system utilizes echocardiographic equipment to transmit and receive the echo signals.

A time series of frames of echocardiographic data is generated. The frames are sets of data points of scalar quantities corresponding to specific sites of the patient's heart. Suitable scalar quantities that bear a specific relationship to physiological dynamics of the heart include mean squared speed, root mean squared speed, mean squared rate of signal change, integrated backscatter, correlation area and echocardiographic data magnitude. For each specific site, the scalar quantity of each frame can be plotted, thereby yielding a plurality of time domain signals with frame-to-frame variations of the selected scalar quantity.

For each time domain signal, a Fourier transform is performed to obtain phase and magnitude data associated with each set of corresponding data points in the time series of frames. For each Fourier transform, the phase identifies the onset of motion at the specific site of the heart associated with the set of corresponding data points from which the Fourier transform was extracted. Optionally, phase angles can be obtained from the time domain signals using processing methods other than Fourier transformation.

Pixel values for imaging the sequence of cardiac operation may then be assigned according to the phase angles. The method and system image the sequence of motion using the pixel values that have been assigned with respect to the various sites of the heart. For example, the pixel values may be gray-scale values that are appropriately arranged to form a single two-dimensional picture. Gray-scale values are assigned from $+\pi$ to $-\pi$, representing black to white, so that an image of a cardiac contraction will include degrees of brightness that increase with the sequence of a cardiac contraction. Cardiac contraction is typically a motion down the septum from the base to the apex of the heart, around the apex, and then up the free ventricular wall. Then the region of the free ventricular wall at the base will be brighter than that of the apex, which in turn will be brighter than the base of the septum.

Alternatively, a dynamic cine loop of image frames is formed, with a pixel of a frame in the cine loop being a particular color, e.g. red, if motion occurred at the cardiac site represented by the particular pixel during or before motion at other cardiac sites in the frame. For example, pixel values may be assigned according to phase values from $+\pi$ to $-\pi$. Individual data points in each frame of the cine loop would then be set to display red, if the data points have a pixel value within a specific window of pixel values. Once set red, the data points may "turn off" in subsequent frames, so that the cine loop displays a wavefront of motion, or the data points may remain red for the duration of the cine loop in order to display motion that has occurred. The window may have a width of $2\pi$ divided by the number of frames in the cine loop, with movement from $+\pi$ to $-\pi$ in order to show forward progression of time. Optionally, the cine loop may be overlaid with a two-dimensional gray-scale image as described above, thereby enhancing anatomic visualization of the cardiac sequence.

As yet another alternative, the phase angles may be retained on a single frame for further analysis that does not necessarily include imaging. For example, the phase angle values themselves may be analyzed by comparing phase angles of regions of interest.

The method and system may be used to monitor operation of the entire cardiac cycle or may be limited to specific cardiac events, e.g. cardiac contraction. However, in limiting the analysis to a specific cardiac event, other major cardiac events are less likely to influence the magnitude and the phase acquired during the process. For example, for a contraction sequence, different hearts with identical systolic contraction sequences may have different characteristics of diastolic filling and atrial kick. The different characteristics will affect the phase of the first harmonic. Such extraneous influences can be precluded by determining phase angles using only the particular cardiac interval of interest. For systolic contraction, the interval should minimally extend from the frame prior to closing of the mitral valve to the frame prior to the opening of the mitral valve.

At times, the selection of an optimal harmonic may be a selection other than the first harmonic. For certain scalar quantities to be monitored, such as mean squared speed, the second harmonic is potentially more useful. The strongest harmonic of a velocity squared curve is theoretically the second harmonic, assuming that the strongest harmonic of the velocity curve plotted over the cardiac cycle is the first harmonic.

An advantage of the present invention is that the sequence of mechanical motion of the heart can be delineated using real-time two-dimensional echocardiography. The regional function of the myocardium can be assessed with an increased degree of reliability. Scalars of mean squared speed, root mean squared speed, mean squared rate of signal change, integrated backscatter, correlation area and echocardiographic data magnitude, when monitored, can be used to form a single two-dimensional image, a dynamic cine loop or phase information for analysis.

BEST MODE FOR CARRYING OUT THE INVENTION

Figure 1:
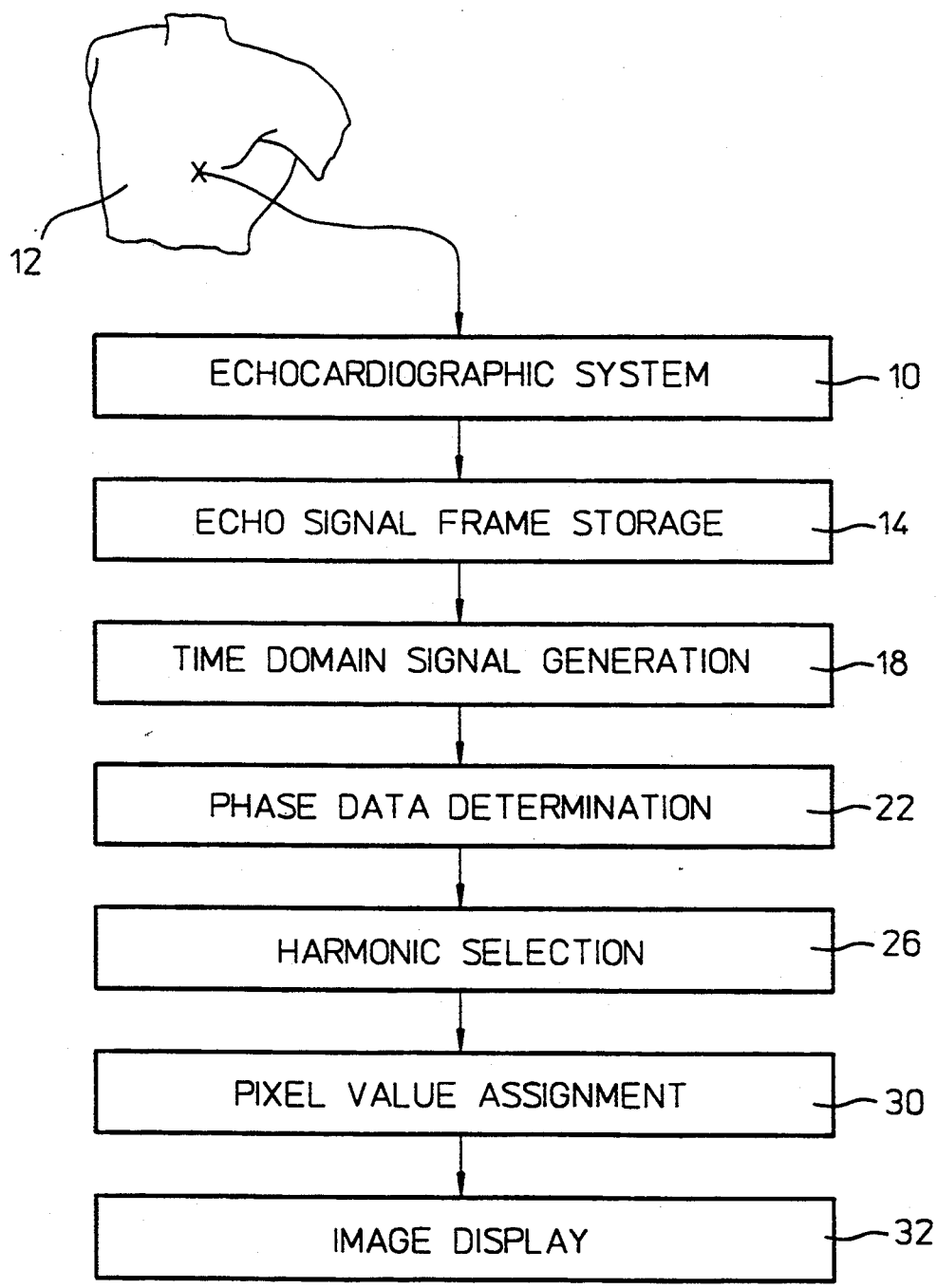
FIG. 1 is a flow chart of a method and system for monitoring and imaging performance of a heart in accordance with the present invention.

With reference to FIG. 1, an echocardiographic system 10 is shown as being utilized to transmit ultrasonic signals and receive ultrasonic reflections from a patient 12. The echocardiographic system is directed to obtain data responsive to operation of the heart of the patient.

Raw data from the echocardiographic system 10 may be processed into the inphase and quadrature (I and Q) components of such data in unscanconverted r-theta format. However, computation in I and Q components is not necessary and in most circumstances is not even desirable. Merely for example, 121 acoustic lines of data are acquired with a spacing of 0.75°, with the first line starting at an angle of $-45°$ from straight ahead. This data may then be scanconverted to x, y coordinate data for processing and viewing. The raw data may be acquired using an echocardiographic system 10 having an array of ultrasonic transducers or a single mechanically scanned transducer.

A critical step is the selection of a scalar for analysis of cardiac operation by phase imaging. A selected scalar should be one that varies predictably with the cardiac cycle, i.e. the scalar and the cardiac cycle should covary. The scalar should also vary with a specific relationship to physiological variables. Possible relationships may be between the scalar and motion of the myocardium or a contractile state of the myocardium. Mean squared speed, root mean squared speed, mean squared rate of signal change, integrated backscatter, correlation area and echocardiographic signal magnitude have been discovered to be the scalars best suited for the method and system to be described below.

Figure 2:
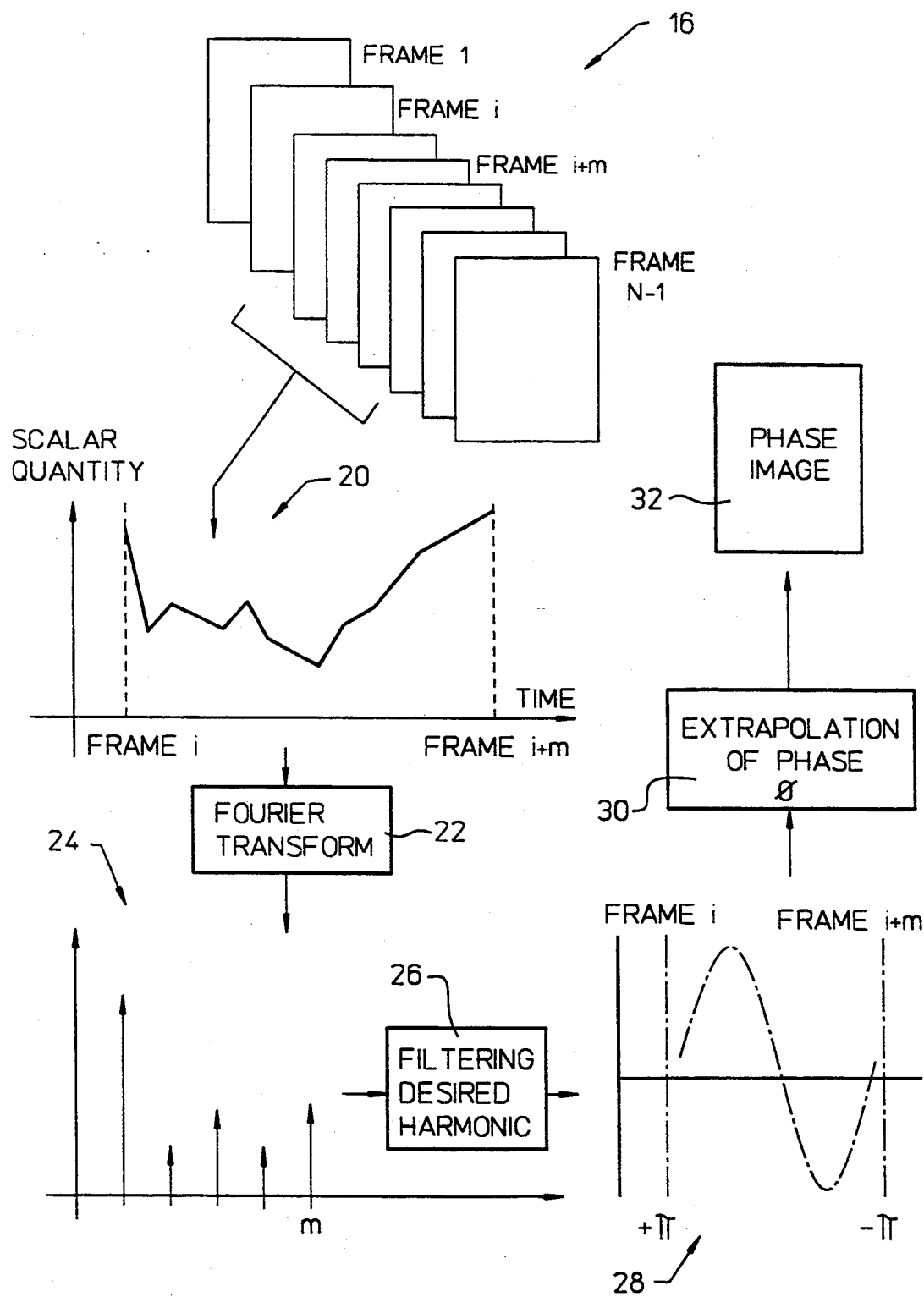
FIG. 2 is a schematical view of the sequence of signal processing for carrying out the system of FIG. 1.

Referring now to FIGS. 1 and 2, a stored time series 16 of frames is shown as starting at Frame 1 and progressing to Frame $N-1$. The time series 16 may be for one or more cardiac cycles. Alternatively, a subset, such as from Frame i to Frame i+m, may be the focus of analysis. For example, the subset may be the systolic interval from the Frame (i) prior to the closing of the mitral valve at the onset of systolic contraction to the Frame (i+m) prior to the opening of the mitral valve at the onset of diastolic filling.

For the desired set of frames, the selected scalar is monitored on a data point-by-data point basis. That is, for each set of data points which corresponds to a specific site of the patient's heart, the scalar quantity is plotted from frame to frame. In FIG. 1, this is shown as time domain signal generation 18, while in FIG. 2 a single time domain signal 20 is shown. Ideally, each data point in a frame within the time series 16 is used in plotting a time-varying signal such as that shown at 20, thereby yielding a number of time domain signals corresponding to the number of data points in a frame. However, the plotting of time-domain signals may be limited to data points corresponding to specified regions of the heart, if desired.

As shown in FIGS. 1 and 2, a Fourier transformation 22 is then performed on each time domain signal 20 to obtain a transform 24 from the particular time domain signal. For the transform 24, each harmonic has an associated magnitude and phase. A filter 26 is then employed to obtain a single phase value and a single magnitude value of the desired harmonic. Typically, the first harmonic is selected since for a given periodic function, the magnitude of the first harmonic is typically largest. However, the present invention is not limited to the selection of the first harmonic. If there is a stronger higher harmonic, such as a second harmonic, it could also be used to ascertain a phase angle. With certain scalars, such as mean squared speed, the second harmonic is potentially very important. Since mean squared speed is a function of velocity squared, the strongest harmonic of the velocity squared curve at 20 is theoretically the second harmonic, assuming that the strongest harmonic of the velocity (unsquared) curve plotted over the cardiac cycle is the first harmonic.

In selecting a harmonic other than the first, the problem of phase wrapping must be considered. For example, where assigned phase values are to be within the range of $-\pi$ to $+\pi$ and the second harmonic is the harmonic of interest, activations that occur at two different times corresponding to $\pi/4$ and $9\pi/4$ will appear to have the same phase of $\pi/4$. Phase unwrapping techniques may be required to decipher a phase portrait generated with a second or higher harmonic.

In the study of cardiac motion, information regarding a particular event of a cardiac cycle is primarily contained during the interval in which the event occurs. However, over the entire cardiac cycle other major cardiac events may influence the magnitude and the phase of the selected harmonic. For example, for two different hearts having the same systolic contraction sequence, the characteristics of diastolic filling and atrial kick may differ, thereby affecting the phase of the first harmonic. One way to preclude such extraneous influences in measuring the cardiac contraction sequence is to limit the monitoring of the selected scalar to the systolic interval from the Frame (i) prior to the closing of the mitral valve at the onset of systolic contraction to the Frame (i+m) prior to the opening of the mitral valve at the onset of diastolic filling.

Data is fit to a wave 28 to delineate the sequence of activity. Thus, a phase angle extrapolation and pixel value assignment 30 is performed on a pixel-by-pixel basis to form a phase image 32. That is, for each time domain signal 20, a pixel value is assigned according to a phase angle extracted by the processing of the time domain signal. Processing by means of Fourier transforms is not critical to the present invention. Other methods of extrapolating a phase angle from the time domain signal 20 are known and may be employed. That is, in FIG. 2, the extrapolation 30 may be performed directly from the signal 20.

Each pixel of the phase image 32 is encoded with its corresponding phase, ranging from $-\pi$ to $+\pi$. The earliest motion is represented by $+\pi$, and the latest motion is represented by $-\pi$. Data acquisition may be gated off the R wave of the ECG complex. An ECG may be used to provide any preliminary information that may be necessary regarding the cardiac cycle and major cardiac events within the cycle, e.g. the onset of systole and diastole.

In one embodiment, the phase image 32 is a frame of data that can be retained for further analysis in order to make determinations regarding operation of the heart. For example, comparisons can be made between the phase angles of different regions of interest.

In another embodiment, the phase imaging 32 may be a display of a single image or may be a dynamic cine loop. A single-image display may be formed by encoding each pixel in the image such that phase values from $+\pi$ to $-\pi$ are displayed from black to white. Since $+\pi$ represents the earliest motion and $-\pi$ represents the latest motion within the time series 16 of echocardiographic data frames, the single-image display 32 of timing will be one in which areas of later activity will be brighter than those of earlier activity. Cardiac contraction is typically a motion down the septum from the base to the apex of the heart, around the apex and then up the free ventricular wall. As such the image will be a gray-scale image in which the free ventricular wall at the base will be shown as being brighter than the apex, which in turn will be brighter than the base of the septum.

Alternatively, the phase image 32 may be a dynamic cine loop of image frames. Individual pixels in a particular frame may be set to a particular color, e.g. red, if the onset of motion of the cardiac site represented by the pixel has occurred during or before motion at other cardiac sites. Where pixel values are assigned according to phase values from $+\pi$ to $-\pi$, the pixels may be set to display red if the pixel values fall within a specific window of pixel values. For example, the window may have a width of $2\pi$ divided by the number of frames in the cine loop, with movement from $+\pi$ to $-\pi$ in order to show forward progression of time. Thus, the number of frames in the cine loop determines the phase resolution and detail obtained in viewing a contraction sequence. Once set red, the pixels may either "turn off" so that the cine loop displays a wavefront of motion, or the pixels may remain red for the duration of the cine loop in order to display motion that has occurred. Optionally, the cine loop may be overlaid with the gray-scale image described above in order to enhance anatomic visualization of the cardiac sequence.

For display purposes, static clutter and other cavity noise may be removed from the phase image 32 by filtering on the magnitude of the signal, filtering on the magnitude of the DC component, or filtering on the magnitude of the first harmonic. In the phase imaging, if the magnitude is less than a predetermined threshold, the phase angle is then suppressed. Generally, the first harmonic filter is better, since noise in the cavity is generally random and typically has no significant first harmonic component, even though it may have a significant magnitude.

As previously noted, the selected scalar for forming the time domain signals 20 of FIG. 2 is preferably directly related to precisely what is being measured, e.g. mean squared speed is directly related to mechanical motion of the heart.

Integrated Backscatter as a Selected Scalar

The echocardiographic system 10 is used to obtain the time series 16 of frames. The echocardiographic system transmits ultrasonic wave energy into the patient 12. The scattering of wave energy by the heart is determined in part by the local variations in density and compressibility of different cardiac regions. It has been determined that physiologic myocardial contraction and relaxation are associated with a parallel, cyclic variation in integrated backscatter; Wickline et al., "The Dependence of Myocardial Ultrasonic Integrated Backscatter on Contractile Performance," *Circulation*, Vol. 72, No. 1, pages 183–192, July 1985.

Analytically, integrated backscatter (IBS) is defined as $$\text{IBS} = \overline{(I^2 + Q^2)},\qquad \text{EQ. (1)}$$

where I is the inphase component and Q is the quadrature component of the echocardiographic signal from the echocardiographic system 10. However, in determining IBS, the I and Q components are not necessarily computed. Integrated backscatter is the equivalent to the square of the magnitude of the echocardiographic signal, averaged over some area or ensemble of data points, as indicated by the bar in EQ. (1). A suitable process would be to square the magnitude data for each data point and then average the squared value with the squared values of adjacent data points in an area or ensemble of data points.

Integrated backscatter covaries with the cardiac cycle in a physiologically significant manner. The work of Wickline et al. has shown that myocardial integrated backscatter, located at mid-myocardium and normal to the line-of-site of interrogation, may be related to the contractile properties of the heart. Integrated backscatter reflects cyclic alterations in myofibrillar elastic parameters, specifically the juxtaposition of intra-cellular and extra-cellular elastic elements that have different intrinsic acoustic impedances and spatial separation. Cardiac cycle-dependent changes in the degree of local acoustic impedance mismatch may thereby cause the changes in the observed backscatter. Integrated backscatter has been shown to vary systematically over the cardiac cycle in normal canine hearts, with the highest values reported near end diastole and the lowest values near end systole.

Echocardiographic Signal Magnitude as a Scalar

The magnitude of the echocardiographic data within the time series 16 of frames is another suitable scalar. Magnitude is the square root of integrated backscatter. Because of this relationship, magnitude will also be related to the contractile state of the heart. The magnitude (E) may be formed from the inphase (I) and quadrature (Q) components of the signal as:

$$E = \sqrt{I^2 + Q^2} \qquad \text{EQ. (2)}$$

Video data for video display is typically calculated by logging and compressing the magnitude data. Standard video data is the data that is often used by researchers who employ "frame grabbers" to digitize two-dimensional frame data or who obtain data from the back-end output of an echocardiographic imaging system. Video data was used in the analysis of the above-identified research periodical of Kuecherer et al.

Correlation Area as the Selected Scalar

Correlation area and integrated backscatter are both related to the contractile state of the heart, thereby providing the desired physiological significance for phase imaging according to FIGS. 1 and 2. The correlation area is a function of the pattern of ultrasonic wave scatterers of the myocardium during an echocardiographic procedure.

For a region of the data set (X) defined over a range ($N_I$ and $N_J$) in the i and j dimensions respectively, the two-dimensional autocorrelation area of X is defined as:

$$\text{Correlation Area} = \frac{\sum_{K=0}^{N_I} \sum_{L=0}^{N_J} C(K,L)}{C(0,0)} \qquad \text{EQ. (3)}$$

where $C(K,L)$ is the two-dimensional autocovariance of the area and is defined as:

$$C(K,L) = \qquad \text{EQ. (4)}$$

$$\left(\frac{1}{N_I - K}\right)\left(\frac{1}{N_J - L}\right) \sum_{i=1}^{(N_1-K)} \sum_{j=1}^{(N_J-L)} (X_{i,j} - \mu)(X_{i+K, j+L} - \mu)$$

where $\mu$ is the mean of X. It then follows that $C(0,0)$ is the autocovariance value of X when $K=L=0$. This is employed in determining the correlation area for purposes of the phase imaging method.

Mean Squared Speed as the Selected Scalar

Mean squared speed is directly related to motion of the heart. Regional speed measurements in real-time echocardiograms are sensitive to all directions of myocardial motion and may be utilized to monitor performance of the heart.

Measuring speed for the purpose of assessing myocardial performance is based on the use of the continuity equation applied to the ultrasonic echoscatter from myocardium. The necessary signals are readily available in standard real-time two-dimensional echocardiographic systems 10 of FIG. 1. Beginning with the echoscatter signal having space and time dependence, $S(x,y,z,t)$, the associated continuity equation is as follows:

$$\frac{dS}{dt} = (\nabla S) \cdot \vec{v} + \frac{\partial S}{\partial t} \qquad \text{EQ. (5)}$$

where v is vector velocity. In ultrasonic echocardiography, $$\frac{dS}{dt}$$

will typically be equal to 0 when there is no sink or source of power during propagation of the return signal. This leaves the following relationship:

$$\frac{\partial S}{\partial t} = -\nabla S \cdot \vec{v} \qquad \text{EQ. (6)}$$

This last equation shows the relationships among the rate of change of signal, $$\frac{\partial S}{\partial t},$$

the spatial gradient, $\nabla S$, and and the vector velocity, v. By forming an ensemble average of the square of the last equation, the mean square rate of change is found:

$$\overline{\left(\frac{\partial S}{\partial t}\right)^2} = \overline{\left(\frac{\partial S}{\partial x}\right)^2} v_x^2 + \overline{\left(\frac{\partial S}{\partial y}\right)^2} v_y^2 + \overline{\left(\frac{\partial S}{\partial z}\right)^2} v_z^2 \qquad \text{EQ. (7)}$$

EQ. (7) shows a relationship between the mean squared rate of change of the signal and the mean squared speed of motion for each direction, $v^2_{(x,y,z)}$, with the mean squared gradient components, $$\overline{\left(\frac{\partial S}{\partial (x,y,z)}\right)^2},$$

as constants of proportionality. The bars in the equation denote an ensemble average. It can be seen that the mean squared rate of signal change provides a relative measure for speed of motion whereby regional deficiencies in myocardial motion can be appreciated in relation to normally moving myocardium.

The gradient components $$\frac{\partial S}{\partial (x,y,z)},$$

are determined by the beam widths and the pulse length of the interrogating transducer, such that the mean squared difference of the backscattered signal is linearly proportional to the mean squared speed components as follows:

$$\overline{\left(\frac{dS}{dt}\right)^2} = \qquad \text{EQ. (8)}$$

$$\frac{\overline{\left(I\frac{dI}{dt} + Q\frac{dQ}{dt}\right)^2}}{I^2 + Q^2} = c\left(\frac{v_x^2}{Y^2} + \frac{v_y^2}{Y^2} + \frac{v_z^2}{R^2}\right)$$

where c is a constant, Y is the beam width, R is the pulse-length of the interrogating pulse, and I and Q are the inphase and quadrature components of the signal. When beam width is equal to pulse length, a spherical interrogation volume is obtained and the mean squared speed can be directly measured using EQ. (7) and (8).

Figure 3:
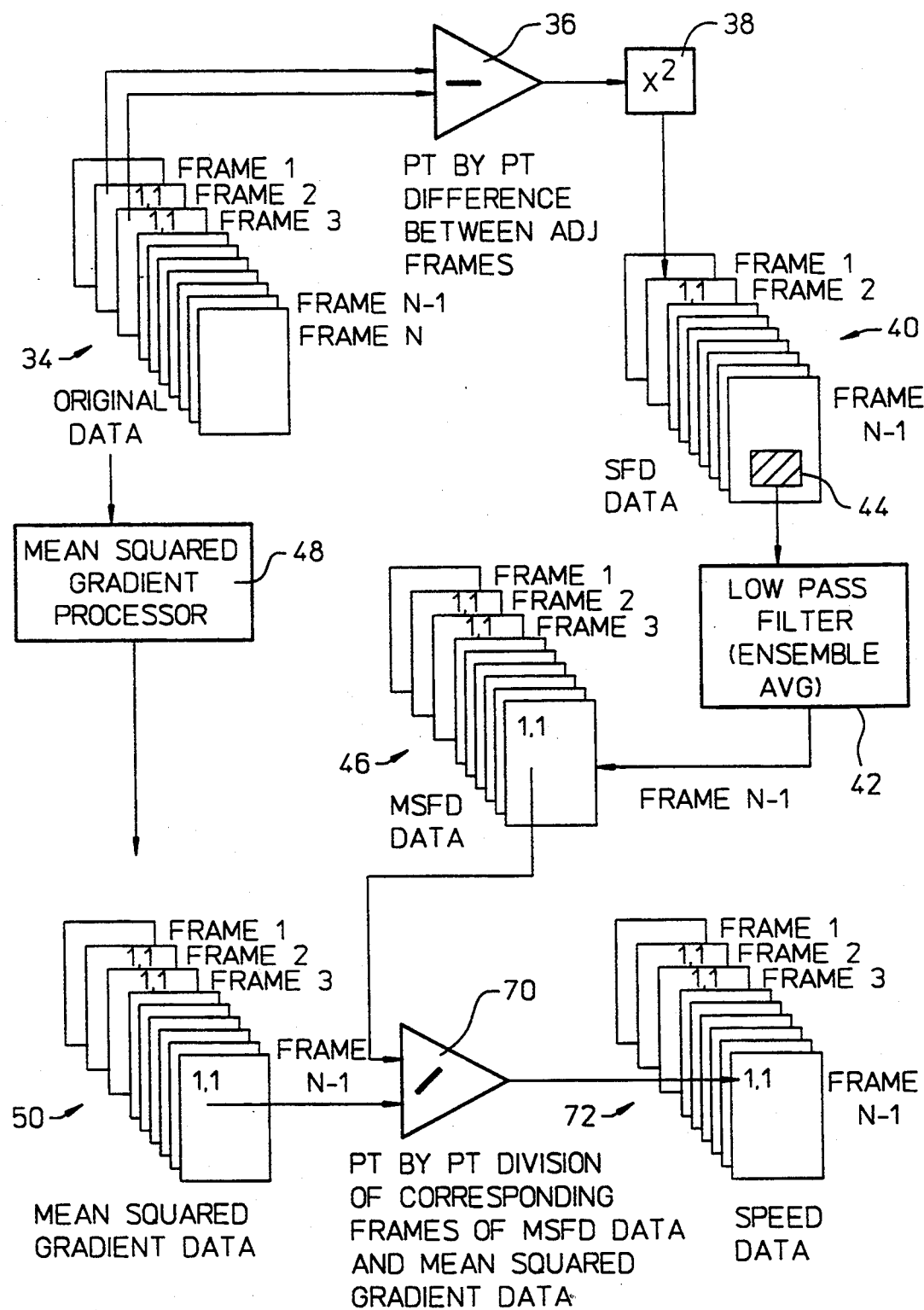
FIGS. 3 and 4 are schematical views for carrying out one embodiment of subprocessing for accomplishing the processing of FIG. 2.

In FIG. 3, a time series 34 of frames of echographic data is formed throughout one or more cardiac cycles. A first processing 36 occurs on a data point-by-data point basis to determine signal change between adjacent frames. In FIG. 3, data point 1,1 of Frame 2 is compared with data point 1,1 of Frame 3 to determine the signal change between the frames at that data point. A second processing 38 squares the difference of signals obtained at the first processing 36. The value of the squared difference is then assigned to data point 1,1 of Frame 2 in a new time series 40. The time series 40 has one fewer frame than the time series 34, since each frame in the second time series is formed by the comparison of two frames in the first time series.

The second time series 40 is a sequence of square of frame differences ("SFD"). Each SFD frame may be low-pass filtered spatially to obtain an ensemble average at 42 for a region 44 of the SFD frame. Thus, each data point is averaged with adjacent data points in the region 44.

The ensemble averaging at 42 is employed to form a third time series 46 on a point-by-point basis. Each frame in the third time series 46 corresponds temporally with a frame in the second time series 40. However, the third time series contains estimates of the mean squared rate of signal change ("MSFD"). Therefore, the frames are a series of functional images of myocardial operation throughout one or more cardiac cycles.

As noted above, the gradient components are related to the beam widths and pulse length of the interrogating transducer. The beam widths and pulse length can be designed to provide respective gradient components which are all the same in a mean squared sense, i.e. the beam widths in azimuth and in elevation are the same and are equal to the pulse length, so that:

$$\overline{\left(\frac{\partial S}{\partial x}\right)^2} = \overline{\left(\frac{\partial S}{\partial y}\right)^2} = \overline{\left(\frac{\partial S}{\partial z}\right)^2}. \qquad \text{EQ. (9)}$$

Figure 4:
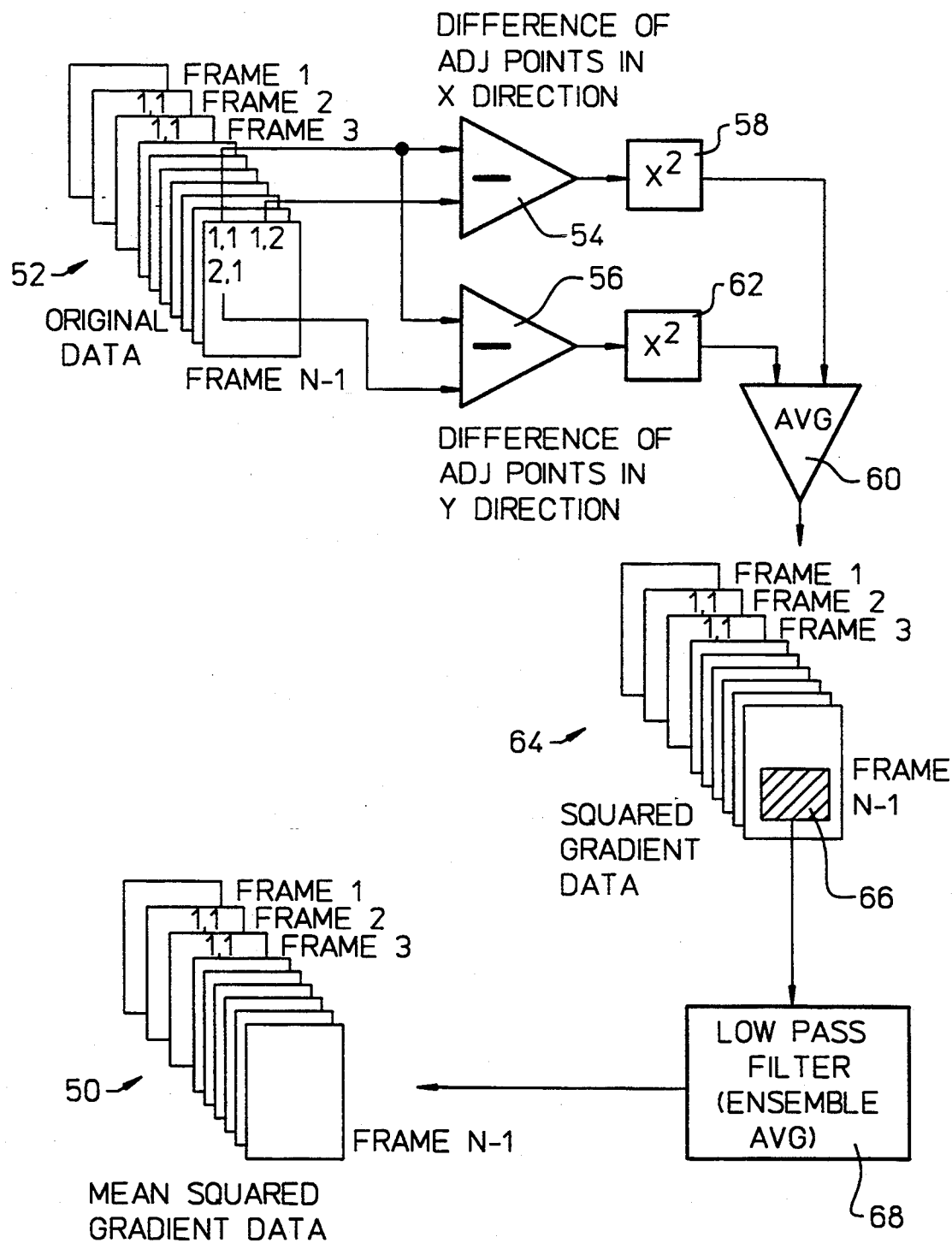

FIG. 3 shows a mean squared gradient processor 48 that is utilized to obtain a fourth time series of frames 50. The fourth time series comprises frames of data related to one or more of the mean squared gradients of EQ. (9). FIG. 4 shows an embodiment of the processor that utilizes changes in both the x direction and the y direction to obtain the mean squared gradient data of the fourth time series of frames 50. The processor begins with frames 52 of original data. The frames 52 may be the same ones as the first time series 34 of FIG. 3, with the final Frame N being disregarded. Alternatively, temporally adjacent frames in the first time series 34 may be averaged on a data point-by-data point basis to reduce the number of frames to N−1.

The mean squared gradient processor 48 includes circuitry 54 for determining the difference between data points of a frame in the x direction. Simultaneously, circuitry 56 determines the difference between adjacent data points in the y direction. The difference value determined at 54 is squared at circuit 58 to provide a first input to a gradient averager 60. A second input to the averager is obtained by squaring the difference value from 56 at a squaring circuit 62.

The output of the gradient averager 60 is employed to form frames 64 of squared gradient data. For each frame 52 of original data, the gradient averaging is carried out in a data point-by-data point manner to generate the N−1 frames 64.

Ensemble averaging takes place at a low pass filter 68 for a region 66 of a selected size. Therefore, each data point in the fourth time series of frames 50 is an ensemble average of a corresponding data point and its surrounding data points from a frame 64.

As previously noted in referring to EQ. (9), in the ideal case, the beam widths and the pulse length of the interrogating transducer can be designed so that all of the gradient components are equal in a mean squared sense. Therefore, in the ideal case the outputs from 58, 60 and 62 are equal. However, the gradient averager 60 may be utilized to reduce the adverse effects of noise generated in non-ideal circumstances.

For FIGS. 3 and 4, the mean squared gradient data of frames 50 will be referred to herein as $$\left(\overline{\frac{dS}{dg}}\right)^2$$

data, which may be determined by a signal change in a single coordinate direction or in more than one direction, as in the embodiment of FIG. 4. In this case, using EQ. (7) and (9) the mean squared speed or root mean squared speed (m) can then be estimated on a data point-by-data point basis by dividing the time-averaged mean squared rate of signal change data of frames 46 by the mean squared gradient data of frames 50, i.e.

$$m = \{|v|^2\}^{0.5} = \left(\left(\overline{\frac{dS}{dt}}\right)^2 / \left(\overline{\frac{dS}{dg}}\right)^2\right)^{0.5} \quad \text{EQ. (10)}$$

The point-by-point division occurs at circuit 70 to generate a fifth time series of frames 72 of speed data.

The fifth time series of frames comprises functional images of mean squared speed or root mean squared speed. Thus, direct quantification of performance is provided.

Referring now to FIGS. 2 and 3, either of the third time series of frames 46 or the fifth time series of frames 72 may be used to obtain the phase image 32 of FIG. 2. That is, the time series 16 may comprise either the frames 46 or the frames 72. The data contained in the time series 16 is analyzed for each data point across the N−1 frames of data or some subset thereof. For each such data point, a time domain signal 20 is obtained and a phase angle is extrapolated from the time domain signal. There are various known methods of extrapolating the phase angle. One such method is to use a Fourier transform 22. As previously noted, the phase image 32 may be a single two-dimensional picture, a dynamic cine loop of image frames, or a frame of data that is retained for further analysis. For example, comparisons of phase angles of different regions of interest can be made.

We claim:

1. A method of monitoring and displaying performance of a heart, comprising the steps of:
coupling echocardiographic probe to a person such that echocardiographic signals reflected from the tissue of heart of said person can be collected;
selecting a cardiac-related scalar quantity for assessing operation of said heart such that said cardiac-related scalar quantity is direction-independent and varies predictably with said performance to be assessed;
monitoring said cardiac-related scalar quantity for various points of said heart tissue for a predetermined time interval, said monitoring including collecting a time series of said echocardiographic signals from said echocardiographic probe and including extracting data from said time series such that a time-varying signal of said cardiac-related scalar quantity is obtained for each of said various points, said monitoring including manipulating data from said echocardiographic signals prior to display in order to extract phase angle data from said time-varying signals; and
displaying said phase angle data such that a sequence of motion of said various points of said heart tissue is exhibited as an indicator of said performance.

2. The method of claim 1 wherein said selecting and monitoring step comprise selecting and monitoring one of mean squared speed, root mean squared speed, mean squared rate of signal change, integrated backscatter, correlation area and the magnitude of echocardiographic data.

3. The method of claim 1 further comprising the steps of:
encoding an image of each of said various points of said heart with a pixel value in accordance with the relative timing of motion determined by extracting said phase angle data; and
forming at least one image based upon said pixel values, thereby forming an image in which relative timing of heart motion can be determined.

4. The method of claim 3 wherein said encoding in accordance with relative timing of motion for each of said various points includes selecting a second harmonic for encoding the various points with a pixel value.

5. The method of claim 3 wherein the step of encoding each of said various points includes a step of assigning gray-scale values based upon phase angle data, said forming at least one image of said relative timing of said heart motion being a step of forming a static image in accordance with said gray-scale values.

6. The method of claim 3 wherein the step of encoding each of said various points includes a step of assigning pixel values based upon whether phase angle data is within a defined range of phase angles.

7. The method of claim 6 wherein the step of forming at least one image includes a step of forming a dynamic cine loop having a plurality of frames such that said defined range of phase angles progressively varies with the formation of said frames in said dynamic cine loop.

8. The method of claim 3 wherein the step of extracting phase angle data includes selecting a harmonic to define a phase angle in the range of $-\pi$ to $+\pi$.

9. The method of claim 1 further comprising analyzing performance of said heart by comparing phase angle data for different regions of interest of said heart.

10. A method of monitoring cardiac performance comprising:
disposing an echocardiographic probe relative to a patient for receiving echocardiographic signals of a selected cardia tissue target volume;
converting said echocardiographic signals into a plurality of data frames of cells of direction-independent values of echocardiographic, said frames thereby forming a sequence of echocardiographic;
storing said data frames in a memory prior to display;
for corresponding cells in said frames of said sequence, determining the onset of change in the direction-independent value in said corresponding cells and representing said onset as a phase angle value; and
representing all said phase angle values in a form for displaying a sequence of motion within said selected cardiac target volume.

11. The method of claim 10 further defined by selecting said direction-independent values from the group of echocardiographic signal characteristics consisting of mean squared speed, root mean squared speed, mean squared rate of signal change, correlation area and the magnitude of said echocardiogram data.

12. A method of monitoring performance of a heart comprising the steps of:
(a) transmitting ultrasonic wave energy into a patient in the direction of the patient's heart;

(b) receiving echo signals reflected from tissue of said heart;

(c) in response to said echo signals, forming a plurality of frames of echo data such that said frames form a sequence generated during a cardiac cycle, said frames having sets of corresponding data points with respect to specific sites of said heart;

(d) for a first set of corresponding data points of said frames, manipulating said echo data generally in the absence of data compensation in order to form a time domain signal of a selected one of mean squared speed, root mean squared speed, mean squared rate of signal change, integrated backscatter, correlation area and echo-signal data magnitude, thereby yielding a time domain signal which varies with frame-to-frame variations of said selected one at said corresponding data points;

(e) extracting motion data from said time domain signal to determine onset of motion with respect to said specific site of said heart represented by said first set of corresponding data points in said frames of step (c);

(f) assigning a pixel value to an image data point of an image to be formed, wherein assigning said pixel value is in response to said motion data;

(g) repeating steps (d) to (f) for each set of corresponding data points to obtain a plurality of said pixel values; and (h) imaging a sequence of cardiac activity utilizing said plurality of pixel values.

13. The method of claim 12 wherein forming said plurality of frames is a step of forming a time series of frames representing an interval not exceeding one cardiac cycle.

14. The method of claim 12 wherein said steps of extracting data from said time domain signal includes determining a phase angle for said first set of corresponding data points.

15. The method of claim 14 wherein assigning said pixel values and imaging said sequence of cardiac activity are steps yielding a dynamic cine loop of image frames.

16. The method of claim 15 wherein forming each image frame in said dynamic cine loop includes selecting a progression of pixel values to be displayed with a progression of said image frames in said dynamic cine loop, said selecting said progression of pixel values including defining a window of phase angles.

17. A system for monitoring performance of a heart comprising:

echocardiographic probe means for transmitting ultrasonic waves into a living body and for receiving echo signals reflected from tissue of said heart;

means for storing a time series of frames of echocardiographic data points in response to echo signals received from said echocardiographic probe means during a predetermined period of time, said means for storing being connected to said echocardiographic means to store echocardiographic data from said probe means;

means for extracting, on a data point-by-data point basis, said echocardiographic data from said recording means to form a plurality of time-varying signals of a cardiac-related, direction-independent quantity of said echocardiographic data;

means for converting each time-varying signal to phase angle data; and means for storing said phase angle data converted from said time-varying signals.

18. The system of claim 17 further comprising means for imaging a sequence of activity of said heart tissue for said predetermined period of time based upon said phase angle data.

19. The system of claim 18 wherein said means for imaging includes a dynamic cine loop of second frames for sequentially displaying said activity of said heart tissue.

* * * * *